United States Patent [19]
Buelna

[11] Patent Number: 5,468,251
[45] Date of Patent: Nov. 21, 1995

[54] SURGICAL SUTURING DEVICE

[75] Inventor: Terry Buelna, Laguna Beach, Calif.

[73] Assignee: Advanced Surgical, Inc., Princeton, N.J.

[21] Appl. No.: 134,561

[22] Filed: Oct. 12, 1993

[51] Int. Cl.$^6$ ................................ A61B 17/00
[52] U.S. Cl. ................ 606/223; 606/139; 606/144; 606/222; 112/169
[58] Field of Search .................. 606/1, 139, 144, 606/147, 148, 222, 223–225; 112/169, 80.03; 223/102–104

[56] References Cited

U.S. PATENT DOCUMENTS

| | | | |
|---|---|---|---|
| 151,179 | 5/1874 | Waldie | 223/102 |
| 818,152 | 4/1906 | Edwards. | |
| 2,516,710 | 7/1950 | Mascolo. | |
| 3,037,619 | 6/1962 | Stevans | 606/148 |
| 4,527,564 | 7/1985 | Eguchi et al.. | |
| 5,037,433 | 8/1991 | Wilk et al. | 606/139 |
| 5,059,207 | 10/1991 | Shah | 606/223 |
| 5,152,769 | 10/1992 | Baber | 606/145 |
| 5,222,951 | 6/1993 | Abidin et al. | 606/1 |
| 5,304,184 | 4/1994 | Hathaway et al. | 606/148 |
| 5,318,577 | 6/1994 | Li | 606/147 |
| 5,320,632 | 6/1994 | Heidmueller | 606/144 |
| 5,336,239 | 8/1994 | Gimpleson | 606/223 |

FOREIGN PATENT DOCUMENTS

| | | | |
|---|---|---|---|
| 893054 | 4/1942 | France | 223/103 |
| 3639489 | 5/1988 | Germany. | |
| 4210724C1 | 7/1993 | Germany. | |
| 166102 | 11/1964 | U.S.S.R.. | |
| 1309971 | 5/1987 | U.S.S.R. | 606/144 |
| 1319836 | 6/1987 | U.S.S.R.. | |
| 1572613 | 6/1990 | U.S.S.R.. | |
| 1396 | of 1910 | United Kingdom | 606/225 |

OTHER PUBLICATIONS

REMA–Medizintechnik GmbH, "Innovation through Progress" 8 pgs.

Primary Examiner—Tamara I. Graysay
Assistant Examiner—Jeffrey A. Schmidt
Attorney, Agent, or Firm—Burns, Doane, Swecker & Mathis

[57] ABSTRACT

An improved device and method for suturing penetrations and incisions through tissue into a body cavity. The device should find particular use in laparoscopic and other types of minimally invasive surgical procedures. A device according to the invention includes a shaft and an inverted needle joined to the shaft. Two ends of a length of suture material are attached at or near a sharpened proximal tip on the needle. The device may include a movable shield that is slidable to alternately cover and expose the sharpened tip of the needle. This shield may include a blunt distal end and an inclined proximal surface to assist the surgeon in guiding the hook into and out of the body cavity. The device may be provided with a visual and tactile indicator on one side of the device to assist the user in threading and removing the suture material into and out of a selected side of the hook.

14 Claims, 8 Drawing Sheets

SURGICAL SUTURING DEVICE

BACKGROUND OF THE INVENTION

FIELD OF THE INVENTION

The invention relates generally to devices and methods for performing surgical procedures. More particularly, the invention provides a device and method for suturing an opening through tissue into a body cavity. The invention will find particular use in laparoscopic and other types of minimally invasive surgery.

Minimally invasive surgery, including laparoscopic, endoscopic, and arthroscopic surgery, is generally performed through small incisions using instruments specially adapted for these procedures. These techniques offer significant advantages over conventional "open" surgery. In particular, trauma to the patient is greatly reduced and recovery times are significantly shorter. For these and other reasons, minimally invasive surgeries are often much less costly than corresponding conventional surgical techniques.

Incisions made while performing minimally invasive surgery can be very small (a few millimeters), or somewhat larger (a few centimeters). Currently, in laparoscopic procedures, incisions larger than about ten millimeters are typically sutured closed after completion of the surgery to prevent herniation. Suturing of such small incisions is problematic, however, for the simple reason that the surgeon can not get his fingers and/or instruments into the incision to suture the incision in the conventional manner.

Suturing of such small incisions is difficult enough in thin patients, and even more difficult in overweight or obese patients. In these patients, the thick layer of fat underlying the skin makes it difficult to reach the fascia, a layer of tough, fibrous tissue through which the suture should be anchored. For these reasons, it would be advantageous to provide special tools and methods to facilitate suturing of surgical incisions made during minimally invasive surgeries.

An existing tool for suturing small incisions is called a Grice needle. This device is a long needle into which a suture can be threaded. The needle is pushed through the fascia on one side of the incision into the patient's body cavity. The suture is then retrieved using a second needle which is penetrated on the opposite side of the incision which has an integral suture snare. Although workable, the use of the Grice needle can be problematic in closing trocar penetrations made in laparoscopic and other minimally invasive procedures, particularly after the viewing scope has been removed. Problems can also arise when the Grice needles are used in blind procedures where the extent of needle penetration cannot be observed.

Another device for suturing percutaneous penetrations is described in a sales brochure published by Rema-Medizintechnik GmbH (Germany). The Rema "Deep Suture" device includes a handle, a control screw, and a shaft upon which a pair of special needles are mounted. Although operation is not clearly described, the device is apparently used by inserting the shaft through an incision and turning the control screw to deploy a pair of needles radially outward so that they lie on opposite sides of the penetration. The device is then hand lifted to penetrate the needles through the fascia from inside the body. The needles are then removed from the handle, and suture extending between the needles pulled and tied to close the penetration.

While perhaps offering some improvement over the Grice needle, the Rema device is less than ideal in some significant respects. First, the Rema device is complex and would be costly to produce. Second, the fixed positioning of the special needles on the shaft limits the surgeon's flexibility in placing sutures around the incision. Additionally, the needles are directed outward in a parallel fashion and exit through the skin. Thus, the surgeon is not able to suture the fascia while allowing the overlying tissue to heal without sutures. The device is likely too expensive to be disposable and must therefore be cleaned and carefully sterilized between uses. Adequate cleaning and sterilization of a surgical device, especially one having a number of recesses in which blood can collect, is often difficult to achieve.

For the reasons noted above, it would be advantageous to provide an improved suturing device and method. Ideally, the improved device would be compact and of simple construction. The device should allow for flexibility in deployment, and in particular should allow the surgeon to suture the fascia layer and/or peritoneum in percutaneous penetrations without suturing the overlying tissue (thus providing a more secure suture with reduced scarring). It would be particularly advantageous if the improved device could be made sufficiently inexpensive to be disposable so that resterilization would not be required.

DESCRIPTION OF THE BACKGROUND ART

A surgical needle having a curved distal end is disclosed in U.S. Pat. No. 818,152. Curved and bent surgical needles are described in the following patents and published applications: U.S. Pat. Nos. 5,152,769; 5,037,433; 4,527,564; and 2,516,710; German Patentschrift 628038 and Offenlegungsschrift 36 39 489; French Patent 455640; and Russian patent publications 1572613, 1319836, and 166102. The Remo-Medizintechnik discussed above is described in a brochure entitled REMA-Innovation through Progress.

SUMMARY OF THE INVENTION

The present invention provides devices and methods for suturing penetrations and incisions made through tissue into body cavities, including percutaneous penetrations and penetrations made through the walls of internal body organs, lumens, and the like. The present invention is particularly useful in laparoscope and other minimally invasive surgical procedures where it may be used for suturing the fascia layer in percutaneous penetrations made for introducing surgical instruments, typically made by the introduction of trocars. The device and method will also be useful in laparoscopic and other endoscopic procedures where the device may be introduced through a trocar for suturing internal tissue target sites.

Devices according to the present invention will comprise an elongate shaft having a proximal end and a distal end, with an inverted needle attached to the distal end of the shaft having a sharpened proximal tip. By "inverted" it is meant that the needle will be pointed or directed toward the proximal end of the shaft, with preferred needles being generally straight (usually over at least 3 cm, and preferably over the proximal-most 4 cm) and usually parallel to the elongate shaft. It will be possible, however, to use needles which are not entirely straight and which deviate somewhat from the parallel orientation, so long as the needle is able to be introduced inwardly through a penetration or incision and thereafter drawn outwardly through the tissue according to the method of the present invention. By "sharpened," it is meant that the proximal tip is tapered, honed, inclined, angled, or otherwise formed to facilitate penetration of the needle through tissue.

The surgical suturing device will carry a length of suture on the needle near the sharpened proximal tip thereof. At least two points on the suture will be removably attached to the needle in a manner such that both ends of the suture may be separately removed from the needle. In this way, the needle can be used to sequentially introduce a first end of the suture through tissue on one side of the penetration and thereafter introduce the other end of the suture through tissue on another side of the penetration without having to withdraw the device from the tissue penetration for reloading. Such methods will be described in more detail below.

Both ends of the suture will be attached to the needle as close as practical to the sharpened proximal tip thereof. Typically, the suture attachment points will be within 5 mm of the proximal tip, preferably being within the 2 mm of the proximal tip and more preferably being within 1 mm of the proximal tip. By locating the suture near the sharpened proximal tip, the suture will be drawn outward through the tissue very shortly after the needle tip emerges therefrom. In this way, the length of the needle can be reduced and the risk of accidental injury from the needle be lessened.

A variety of anchors can be used for removably attaching the suture ends to the inverted needle. In the exemplary embodiments, apertures or "eyes" are provided in the body of the needle immediately distal to the sharpened proximal tip. In the simplest case a single aperture or eye is provided, where both ends of the suture are drawn through the eye, preferably in opposite directions so that removal of the first suture end will not dislodge the second suture end. Preferably, a pair axially spaced-apart apertures are provided, with one end of the suture passing through each aperture. The two apertures permits the suture ends to be oriented on the same side of the needle, facilitating manipulation by the physician. Other suitable anchors include slots, cleats, adhesives, fasteners, and combinations thereof.

The inverted needle may be attached to the elongate shaft in any manner which holds the needle in the desired orientation. Typically, the inverted needle will be fixedly attached to the shaft, but in certain circumstances, it may be possible to use a needle which is removably attached. In the first exemplary embodiment of the device of the present invention, the inverted needle is formed from a continuous length of needle stock, typically a narrow gage stainless steel rod, with a junction region formed at the distal end of the device. The junction region may have a J-shape, a V-shape, or any other geometry which provides for the desired orientation. In a second exemplary embodiment, the inverted needle comprises a separate needle assembly which is attached at the distal end of a generally straight shaft body. The needle assembly includes three segments, with a lateral segment joining the inverted needle segment to a first axial segment which is attached directly to the shaft. It will also be possible to stamp the needle from flat metal stock and form the needle from plastics using conventional fabrication techniques.

In a preferred aspect of the present invention, a shield is provided for selectively covering the sharpened needle tip. In particular, it is desirable to cover the needle tip after both ends of the suture have been penetrated through tissue and the device must be withdrawn through the initial penetration which is to be closed. By covering the sharpened proximal tip of the inverted needle, accidental needle penetration can be avoided. Optionally, the needle tip may also be covered while the device is being introduced inwardly through the tissue incision or penetration. An exemplary shield structure is mounted on the shaft to axially slide between a first position in which the sharpened tip is exposed and a second position in which the sharpened tip is covered. Preferably, the shield includes a proximal surface which is inclined or canted away from the shaft to facilitate withdrawal of the device through the tissue penetration when the shield is in its second position, and a curved or blunt distal surface to facilitate introduction of the device.

In another aspect of the present invention, the surgical suturing device is provided with the suture preattached to the inverted needle in the manner just described. Typically, the combination of surgical suturing device and suture will be sterilized and disposed within a sterile package, such as a sterilized pouch.

In another particular aspect of the present invention, the needle will be generally straight and preferably have a length in the range from about 1 cm to 8 cm, preferably from 3 cm to 5 cm. The needle will also be generally parallel and laterally spaced apart from the shaft, typically by a distance in the range from about 3 mm to 15 mm, preferably from 5 mm to 10 mm.

According to the method of the present invention, the suturing device is first inserted through the tissue penetration and positioned so that the sharpened proximal tip of the inverted needle is at a first target side on one side of the penetration. The inverted needle is then drawn outwardly through the tissue so that its proximal tip carrying the suture emerges therefrom. In the case of suturing the fascia layer in a percutaneous penetration, the needle will be drawn out through the tissue just above the fascia layer and within the region of the penetration which lies in the subcutaneous layer. After removing a first end of the suture from the inverted needle, the distal end of the device is passed back through the penetration and the sharpened proximal tip positioned at a second target side on another side of the penetration. The device is again drawn outwardly so that the needle carrying the suture passes through the tissue, emerging at a desired location. The second end of the suture is then removed from the needle, and the first and second suture ends may be secured to close the penetration, typically by tying or optionally using some clamp or other fastening means for securing.

After removing the second end of suture from the inverted needle, the device must be withdrawn from the tissue penetration. Typically, this will be achieved by retracting the device through the penetration a third time so that the needle is withdrawn from the posterior surface of the tissue being sutured. The entire device may then be withdrawn through the penetration, preferably with the needle being covered by the shield. The device could be withdrawn, however, in other ways. For example, by using a removable needle, the needle could be detached from the shaft after or concurrent with the removal of the second end of suture. The remainder of the device could then be withdrawn from the penetration without concern over accidental needle penetration.

DESCRIPTION OF SPECIFIC EMBODIMENTS

The invention provides an improved device and method for suturing openings and incisions through tissue into a body cavity of a patient. Most often, the device and method will be used for suturing percutaneous penetrations where the suture may be anchored in the underlying fascia layer. The device and method may also be used for suturing penetrations in internal body organs and structures. The device and method will find particular use in minimally invasive surgery including laparoscopic, endoscopic and arthroscopic surgeries.

Figure 1:
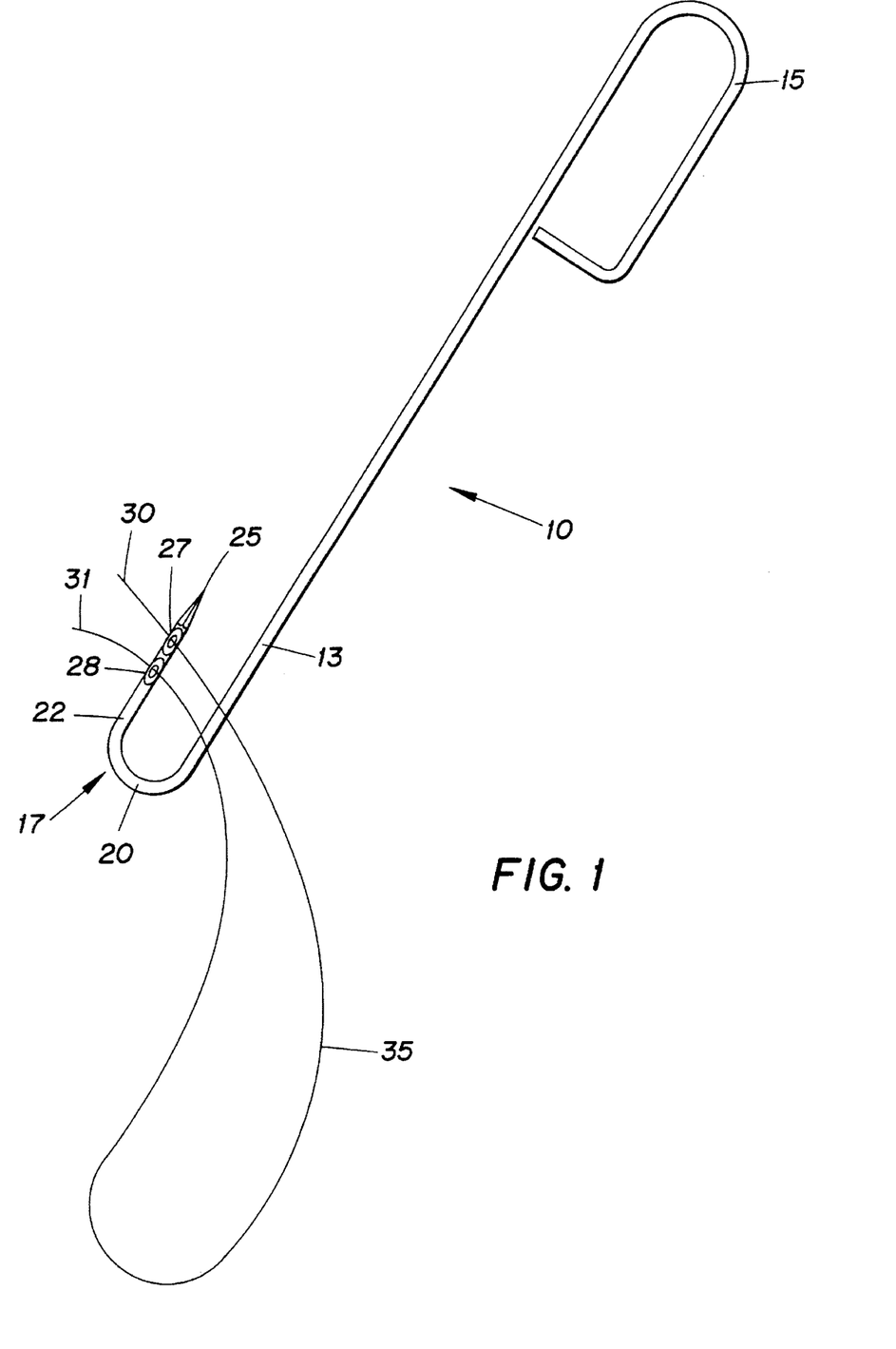
FIG. 1 depicts a first embodiment of a suturing device constructed according to the present invention.

A first embodiment of a surgical suturing device 10 constructed in accordance with the principles of the present invention as illustrated in FIG. 1. The suturing device 10 includes shaft 13 having a handle 15 at its proximal end and a needle assembly 17 at its distal end. The needle assembly 17 includes an inverted needle 22 having a sharpened proximal tip 25 and is connected to the shaft 13 by a lateral segment 20. A pair of axially spaced-apart apertures 27 and 28 are formed in the needle 22 immediately distal to the sharpened proximal tip 25. First end 30 and second end 31 of the length of suture 35 are secured within the first aperture 27 and second aperture 28, respectively.

The suturing device 10 may be formed from a single length of stainless steel or other medically acceptable needle stock. The device 10 may be constructed simply by bending needle stock into the illustrated geometry. Typically, the overall length of the device will be in the range from 10 cm to 40 cm, preferably from 25 cm to 30 cm, with the needle 22 having a total length from the distal end of the device to the proximal tip 25 of the needle in the range from 1 cm to 8 cm, preferably from 3 cm to 5 cm. The needle will usually be oriented parallel to the axis of shaft 13 and be laterally spaced-apart therefrom by a distance in the range from 3 mm to 15 mm, preferably from 5 mm to 10 mm.

Figure 1A:
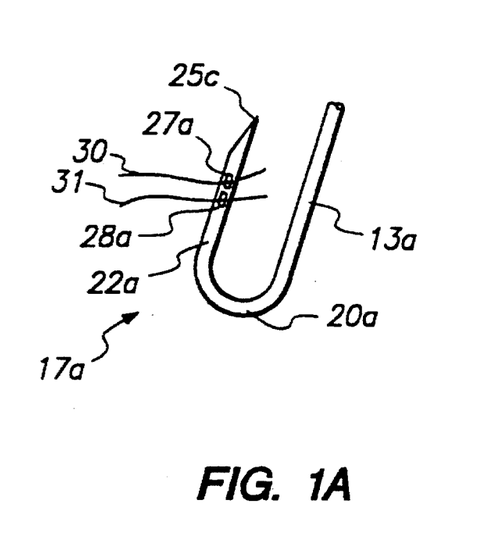
FIGS. 1A–1D illustrate alternate distal constructions for the device of FIG. 1.

It will be appreciated, however, that the geometry of the needle assembly 17 may vary and that the particular suture anchor(s) provided on the needle may differ. For example, FIG. 1A illustrates a J-shaped needle assembly 17a having a pair of suture-receiving slots 27a and 27b. The slots may be machined into the side of the needle, e.g., by electrical discharge machining methods or by stamping.

Figure 1B:
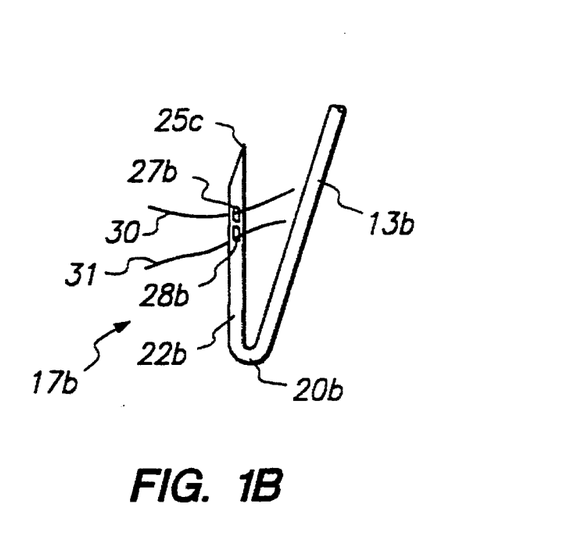

FIG. 1B illustrates a second alternative needle assembly 17b having a V-shaped geometry. While the inverted needle 22b will not be parallel to the axis of shaft 13b, the inclined needle orientation may be useful in certain procedures.

Figure 1C:
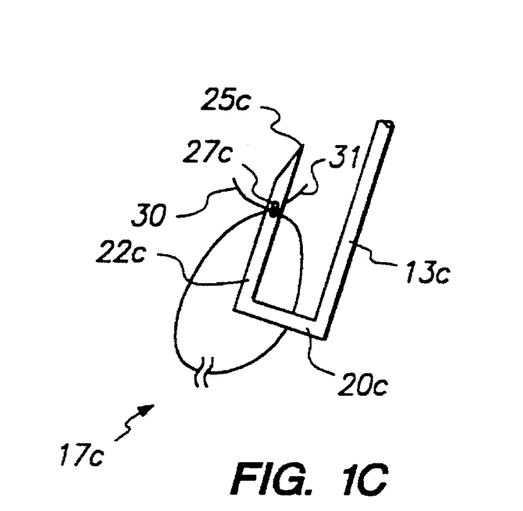

Yet a third alternative of a needle assembly 17c is illustrated in FIG. 1C. Needle assembly 17c includes a straight lateral element 20c joining shaft 13c to inverted needle 22c. Needle 22c includes a single aperture 27c located just distally of the sharpened proximal tip 25c. Suture ends 30 and 31 are crossed within the aperture 27c so withdrawal of the suture end 30 will not accidently dislodge the second end 31. It should be appreciated, of course, that other measures could be taken for isolating the suture ends within a single aperture. The primary requirement of the present invention is that the suture ends be secured to the inverted needle just distally of its sharpened proximal tip in an manner so that each suture end may be removed separately from the needle without dislodging the other suture end. Any design which achieves that objective would be suitable for the anchor(s) of the present invention.

Figure 1D:
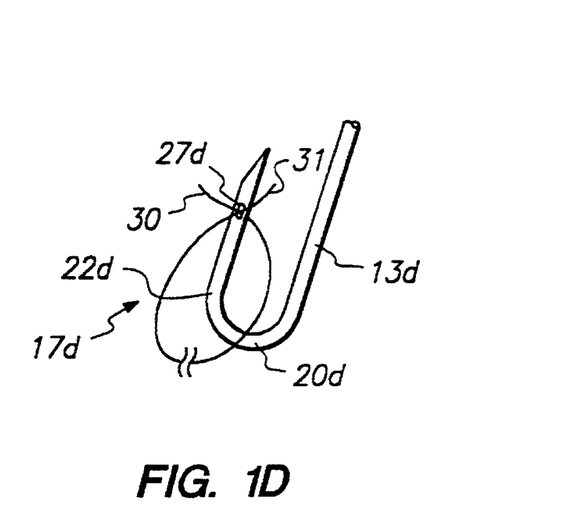

FIG. 1D illustrates a needle assembly 17d having a curved profile, similar to assemblies 17 and 17a, and including a single aperture 27d having suture ends 30 and 31 crossed therein.

Figures 2, 3A:
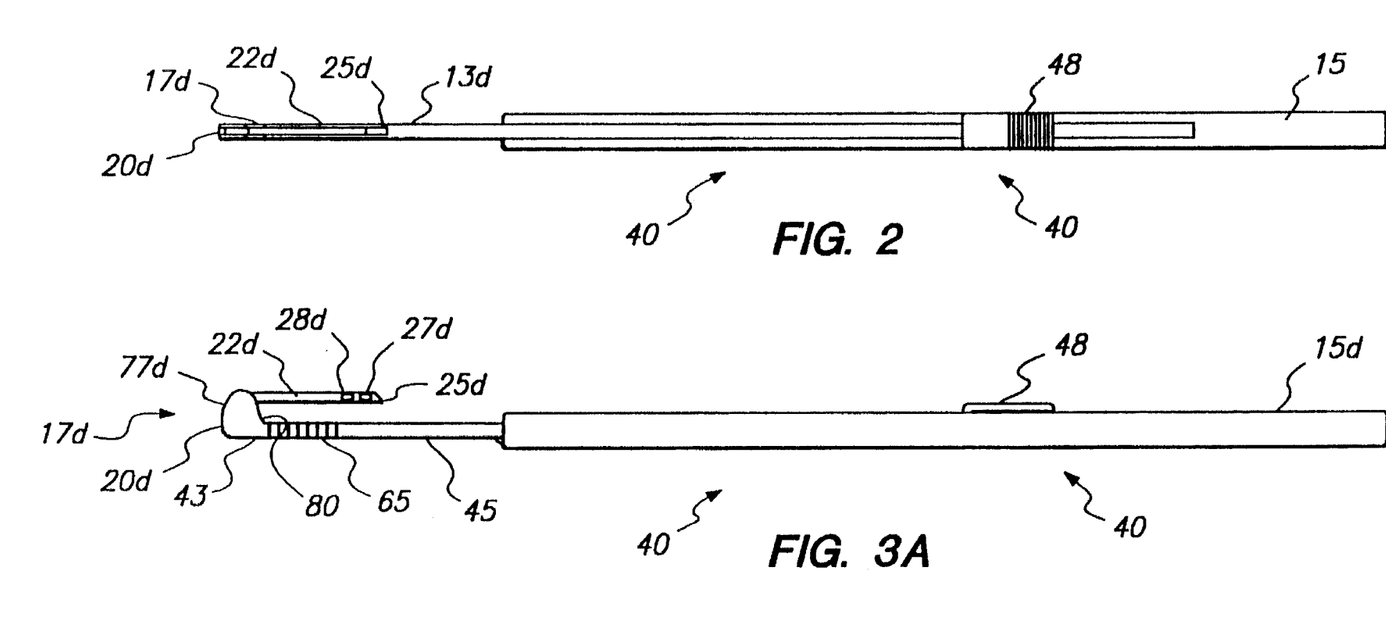
FIG. 2 is a top view of a more advanced embodiment of the suturing device.
FIG. 3A provides a side view of the device of FIG. 2 with a needle shield extended.
Figure 3B:
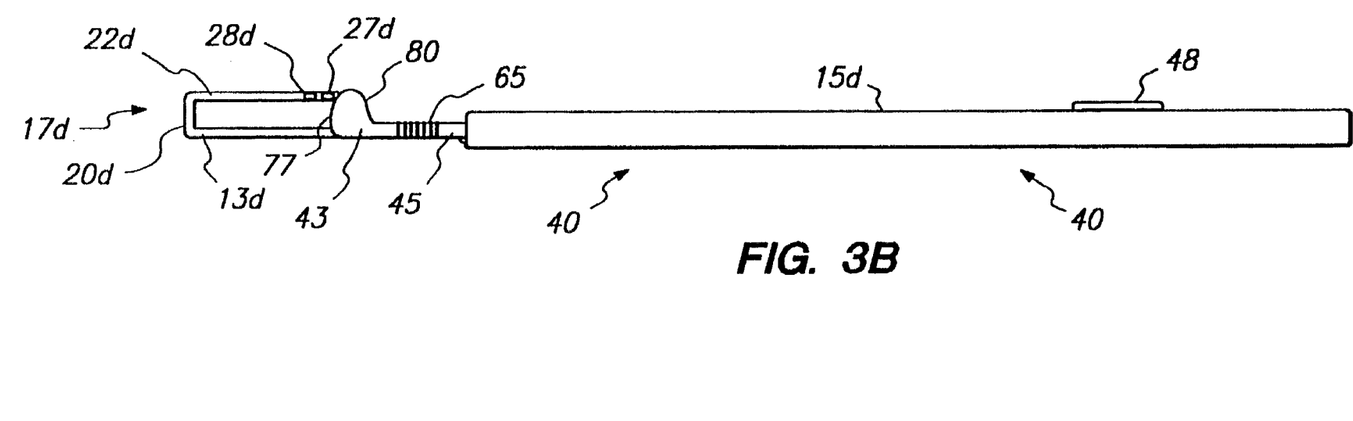
FIG. 3B provides a side view of the device of FIG. 2 with the needle shield of FIG. 3A retracted.

A second embodiment 40 of a device according to the invention is depicted in FIGS. 2, 3A and 3B. FIG. 2 provides a top view of the device, FIG. 3A is a side view showing a shield 43 extended distally to expose sharpened tip 25d of 17d, and FIG. 3B is a side view with shield 43 retracted to cover the sharpened tip 25d. For convenience, elements in FIGS. 2, 3A, 3B, and 4 which are analogous to elements of the device 10 of FIG. 1 will be given identical reference numbers with the suffix d.

As can be seen in these views, the device 40 comprises a shaft 13d fitted with a handle 15d, and a needle assembly 17d comprising a lateral section 20d, an inverted needle 22d and the sharpened proximal tip 25d. Like the first embodiment 10 depicted in FIG. 1, the second embodiment has two spaced-apart anchors, i.e. apertures 27d and 28d, disposed immediately distal to the sharpened proximal tip 25d of the needle 22d.

Unlike the embodiment of FIG. 1, however, the second embodiment includes shield 43 slidably mounted on the shaft 13d. Shield 43 is connected by means of a link 45 to a slide 48 so that the shield may be retracted and extended by manual actuation of the slide 48 by the surgeon. Shield 43 is movable between a first position in which the sharpened proximal tip 25d of the needle 22d is exposed (FIG. 3A) and a second position in which the sharpened proximal tip is covered (FIG. 3B).

The device 40 further includes a set of ridges or serrations 65 on link 45 of shield 43. These serrations provide a visual and tactile indicator to the surgeon to indicate which side of the device the suture is loaded on (in order to permit quick identification of the side from which to remove the suture). The suture ends are preferably threaded into and withdrawn from the side of the hook on which the indicator is located.

Usually, the suture 35 will be preloaded onto the suturing device 40, and the construction of device and suture placed in a sterilized pack. A particular advantage of the present invention is that the fabrication cost is sufficiently low so that the device may be disposable. The device, however, may be reusable, in which case the needle 22d will have to be rethreaded with suture as illustrated.

The individual parts of the device may be formed of a variety of materials having suitable properties. For example, the needle assembly 17d and shaft 13d may be formed of surgical stainless steel. Shield 43, link 45 and slide 48 can be made of a medical grade polycarbonate plastic such as LEXAN® (General Electric Plastics). Finally, handle 15d can be made of a medical grade ABS plastic such as CYCOLAC® (General Electric Plastics). For reusable products, it is best if all components can withstand high temperatures to permit autoclaving.

It will be appreciated that the geometry of the needle assembly 17d may be varied as described above in connection with the needle assembly 17 of the surgical suturing device 10. That is, the needle 22d will preferably be straight, but may have some degree of curvature or other deviation so long as it does not inhibit tissue penetration and withdrawal according to the method of the present invention, as described hereinafter. The needle 22d will also usually be oriented parallel to the shaft 13d, but may deviate so long as the ability to utilize the needle is not significantly compromised. Similarly, a wide variety of suture anchor(s) may be used together with or in place of the apertures 27d and 28d.

In addition to variations in the structure of needle assembly 17d, the structure of the needle shield 43 may also be varied in any manner consistent with its primary requirement, i.e. the ability to selectively cover the sharpened proximal tip 25d so that the tip may be exposed when tissue is being penetrated to introduce suture and may be covered when it is necessary to withdraw the device 40 to remove the needle assembly 17d through the penetration without accidental needle penetration.

An exemplary method for suturing with either the first device (FIG. 1) or the second embodiment (FIGS. 2, 3A and 3B) is illustrated in FIGS. 4–9. Note that these figures depict the method as performed with the second embodiment 40.

Figure 4:
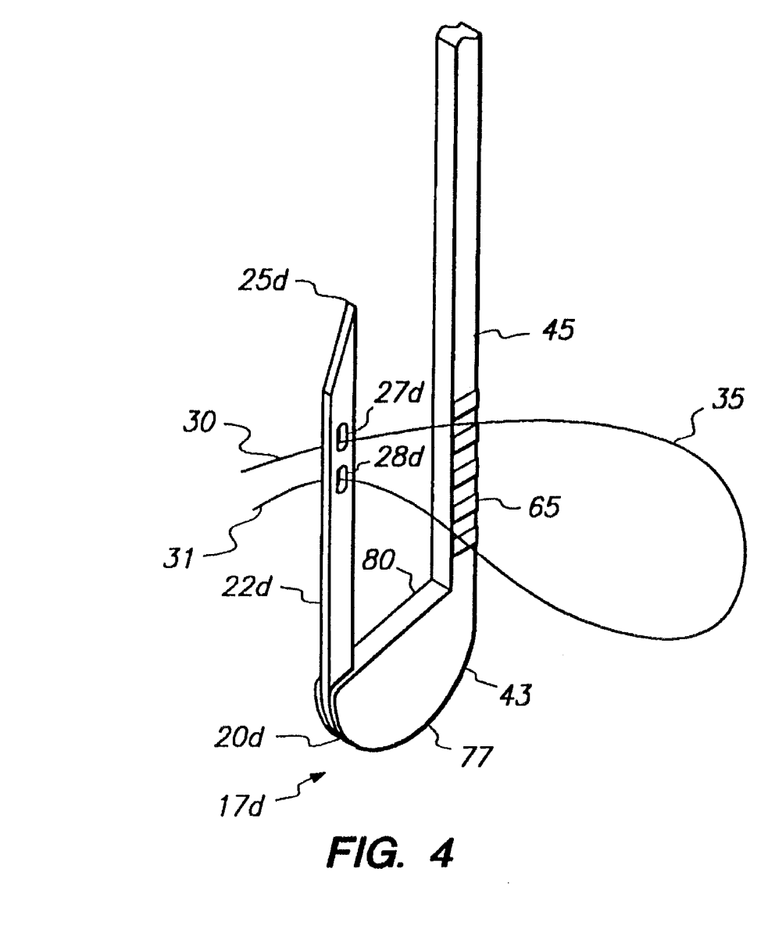
FIGS. 4–9 illustrate use of the device of FIGS. 2, 3A and 3B in an exemplary method for using the device according to the present invention.
Figure 5:
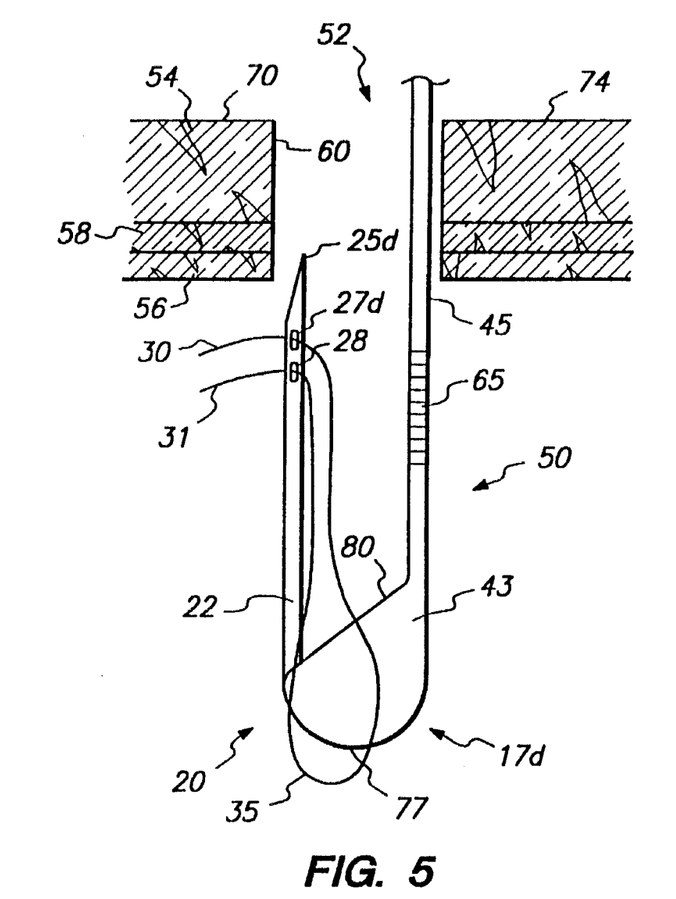

With shield 43 extended as depicted in FIG. 4, i.e, with sharpened tip 25d of needle assembly 17d exposed, suture material 35 is loaded (if necessary) into the device by threading first and second ends 30 and 31 through eyes 27d and 28d on needle 22d. After suture material 35 is loaded into needle 22d, the hook and the suture material are inserted into a body cavity 50 through a percutaneous penetration 25 in tissue 54 as illustrated in FIG. 5. Optionally, the shield 43 may be retracted proximally to cover the needle tip 25d during insertion. Tissue 54 comprises three layers, the peritoneum 56, the fascia 58, and the subcutaneous layer 60.

Figure 6:
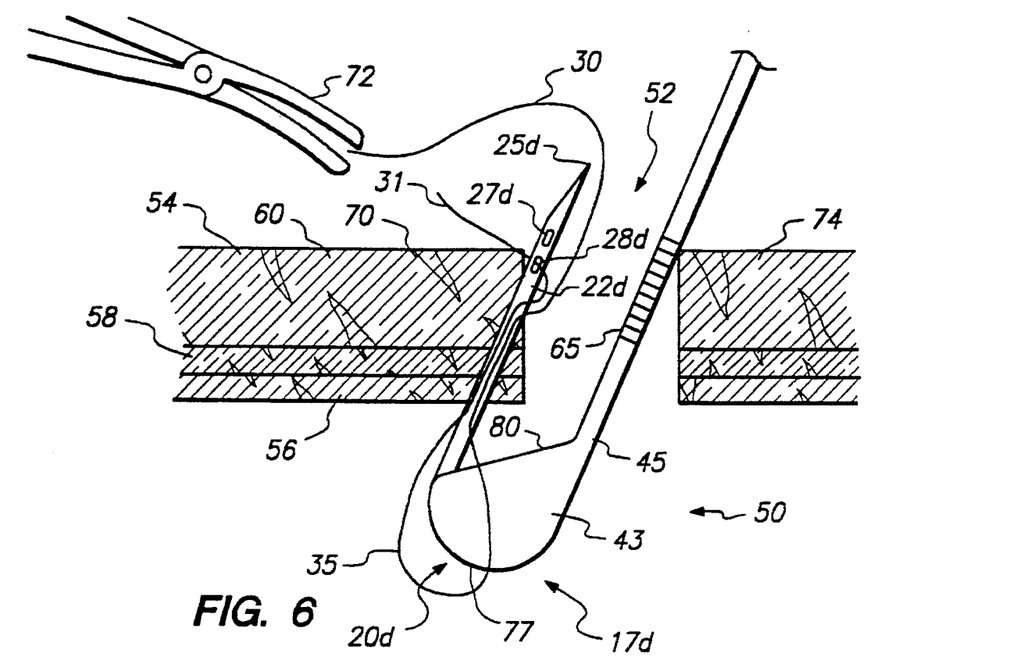

Referring now to FIG. 6, the sharpened proximal tip 25d of needle 22d is pulled up to create a first penetration on a first side 70 of the percutaneous penetration 52. The needle 22d is drawn up through peritoneum 56, fascia 58, and at least a portion of subcutaneous layer 60. This draws first end 30 of suture material 35 out of body cavity 50. The first end 30 is then removed from the first eye 27d and secured with a clamp 72.

Figure 7:
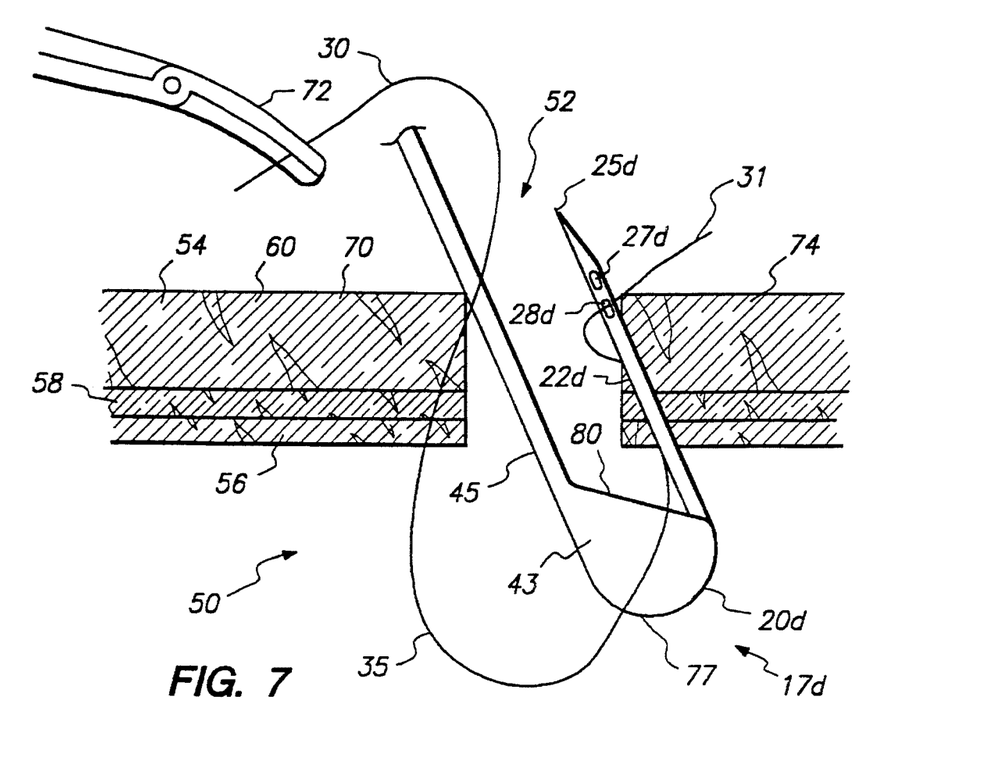

Referring to FIG. 7, the distal end of the device including needle assembly 17d is then pushed back into the body cavity through the first penetration, rotated to a second side 74 of penetration 52, and pulled back out of the body cavity to form a second penetration through at least a portion of the second side of the tissue including fascia 58. The second end 31 of suture material 35 should be pulled through peritoneum 56, fascia 58 and at least a portion of subcutaneous layer 60.

Figure 8:
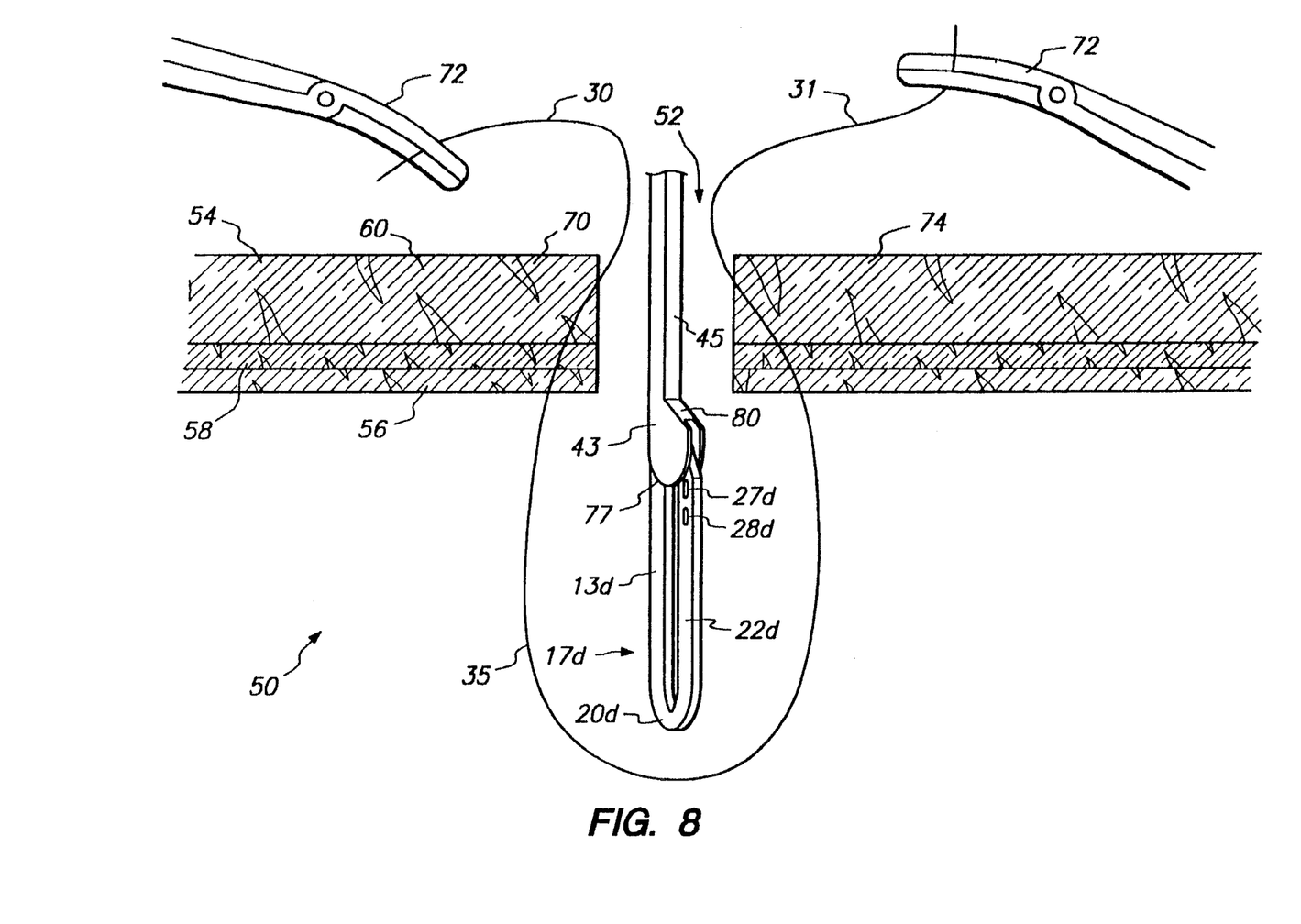

As depicted in FIG. 8, the second end 31 of the suture material is removed from the needle 22d and clamped, and the needle is pushed back through the second puncture into the body cavity 50. Shield 43 is then shifted to cover the sharpened tip 25d of the needle 22d so that the needle may be withdrawn safely from the body cavity through the percutaneous penetration without danger of puncturing or snagging the tissue at the sides of the penetration.

Figure 9:
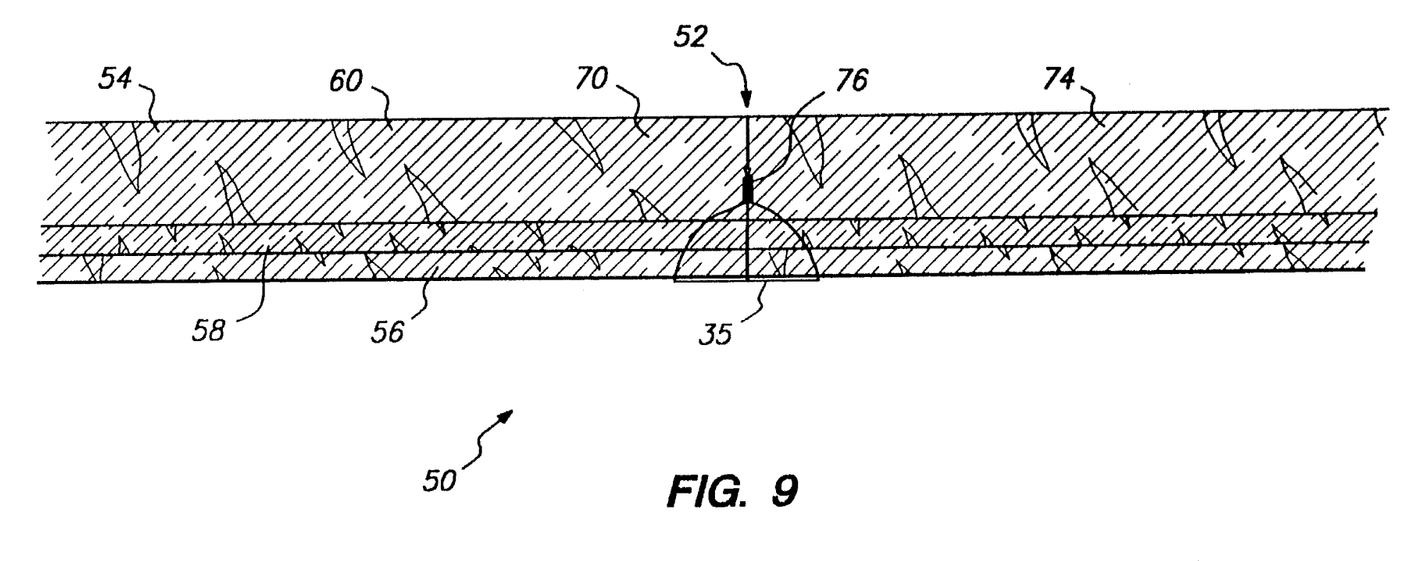

Finally, as depicted in FIG. 9, the ends of suture material 35 are drawn tight to close the incision. A knot 76 is tied by the surgeon to secure the ends of the suture, and the remaining loose ends are clipped and discarded. The penetration will thus be able to heal quickly with minimum scarring since the suturing penetration beneath the skin. By drawing the suture ends back through the sides of the tissue, i.e., through the sides of the subcutaneous layer as depicted in these figures, rather than completely through the top skin layer of the tissue, the penetration may be closed without the deformation and scarring that might otherwise result. The suture should be drawn completely through the fascia layer, however, as this tough and fibrous layer of tissue makes a good anchor for a high strength suture, preventing herniation of tissue.

Referring back to FIGS. 3A and 3B, the shield 43 of the depicted embodiment is provided with surfaces providing functional advantages during use of the device. Referring specifically to FIG. 3A, when shield 43 is extended, a bottom surface 77 of the shield presents a curved leading edge which minimizes the risk of trauma as the needle assembly 17d is inserted though the penetration into the patient's body cavity (see FIG. 5). Of course, other tapered and/or blunt geometries could be selected for the leading edge to minimize the risk of trauma, as just described. Thus, with the protective shield 43 extended distally, the lateral element 20d will be covered so that its geometry is not critical.

Referring now to FIG. 3B, shield 43 may be further provided with an inclined or canted top surface 80. When the shield is in its retracted position covering the hook, top surface 80 slopes away from shaft 13. This is advantageous since it reduces snagging and facilitates the smooth withdrawal of the device from the patient's body cavity near the end of the procedure (see FIG. 8).

Figure 10:
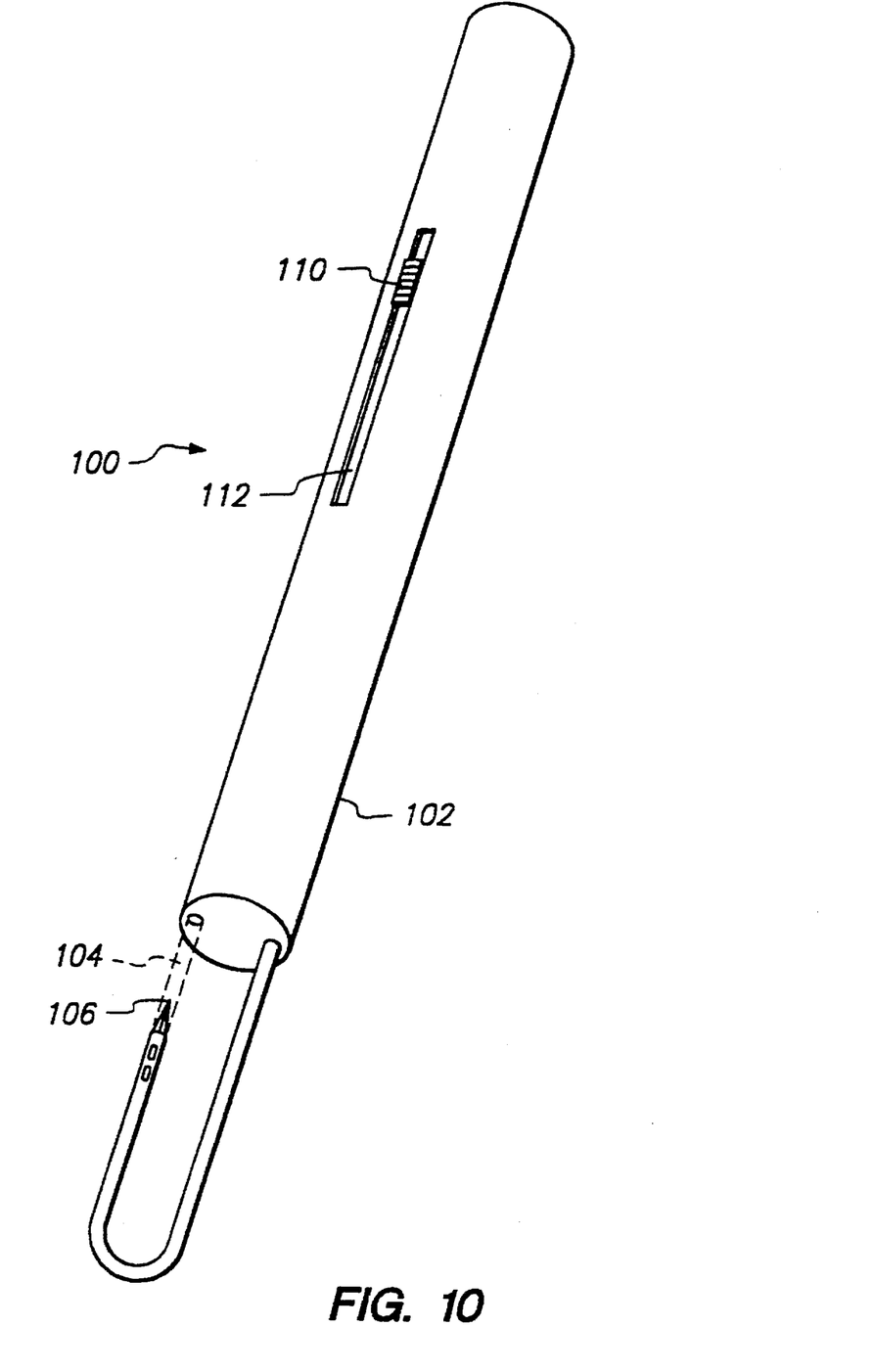
FIG. 10 illustrates a third embodiment of a suturing device constructed according to the present invention.

FIG. 10 illustrates an alternate embodiment 100 of the device of the present invention. The device 100 differs from the previous embodiments in several respects. First, a cylindrical body 102 is sized so that it can be introduced through a conventional trocar, typically having a nominal outer diameter of 5 mm or 10 mm, corresponding to conventional trocar lumen sizes. By providing such a cylindrical body 102, the trocar could be removed over the device 100, and the device body 102 will substantially occlude the tissue puncture site, limiting bleeding and maintaining insufflation. It would further be possible to reintroduce the trocar over the device 100 to regain access to the puncture site for any reason.

A second modification in device 100 is a shield 104 which is extended distally to cover tip 106 of needle assembly 108, as illustrated in broken line. The shield 104, in turn, is actuated by thumb slide 110, which is recessed in a slot 112 formed in the side of body 102. In this way, the slide 112 does not interfere with introduction of the device 100 through a trocar.

Other possible modifications of the device include a collar or ring which may be mounted about the shaft of any of the devices heretofore described and illustrated. The collar or ring could be formed to engage and seal against a tissue puncture site to staunch bleeding and/or maintain insufflation.

Two embodiments of devices according to the invention, as well as a specific method for using the devices, have been described in detail. However, modifications and variations may occur to those skilled in the art without departing from the principles of the claimed invention. Therefore, the scope of the invention should be determined primarily with reference to the appended claims, along with the full scope of equivalents to which those claims are entitled by law.

What is claimed is:

1. A method for suturing a tissue puncture site, said method comprising:

provided a suturing device having an inverted needle at its distal end, and a length of suture removably attached at opposite ends thereof near a sharpened proximal tip on the needle;

inserting the distal end of the device through the puncture site and positioning the sharpened tip at a first target site on one side of the puncture site;

drawing the needle outward through the tissue and removing a first end of the suture therefrom;

reinserting the distal end of the device through the puncture site and positioning the sharpened tip at a second target side on another side of the puncture site;

drawing the needle outward through the tissue and removing a second end of the suture therefrom; and securing the first and second suture ends to close the puncture site.

2. A method as in claim 1, further comprising reinserting the distal end of the device through the puncture site after the second end of the suture has been removed from the needle, covering the sharpened proximal tip of the needle with a shield, and withdrawing the distal end of the device outward through the puncture site with the sharpened tip covered.

3. A method as in claim 1, wherein the puncture site is a percutaneous puncture site and the method includes drawing the needle outward through the fascia layer and subcutaneous layer into the puncture site.

4. A method as in claim 1, further comprising securing the suture ends within the puncture site beneath the skin.

5. A method as in claim 1, wherein the tissue puncture site is in an internal body structure and the method includes disposing the suturing device in a trocar.

6. A surgical suturing device comprising:

an elongated shaft having a proximal end and a distal end;

an inverted needle attached to the distal end of the shaft and having a sharpened proximal tip;

a pair of spaced-apart apertures located on the needle immediately distal to the sharpened tip for separately securing opposite ends of a length of suture thereto, wherein one end of suture can be removed from the needle without dislodging the other end of suture;

a shield slidably mounted on the shaft, the shield being movable along the shaft between a first position in which the sharpened tip is exposed, and a second position in which the sharpened tip is covered by the shield: and a slide slidably disposed near the proximal end of the shaft and connected to the shield, wherein the shield is movable between the first and second positions by movement of the slide, the shield being movable proximally from the first position to the second position by proximal translation of the slide.

7. An assembly comprising;

a length of suture; and a surgical suturing device comprising an elongate shaft having a proximal end and a distal end, an inverted needle attached to the distal end of the shaft and having a sharpened proximal tip, and a pair of spaced-apart apertures located on the needle within 5 mm of the sharpened tip for attaching at least two ends of the suture thereto;

wherein the suture extends through at least one of the apertures in a manner such that one end of the suture can be removed from the needle without dislodging the other end of the suture.

8. An assembly as in claim 7, further comprising a sterile package for holding the suture and the suturing device.

9. An assembly as in claim 7, wherein each suture end is separately held in one of the two apertures.

10. A surgical suturing device comprising:

an elongated shaft having a proximal end and a distal end;

an inverted needle attached to the distal end of the shaft and having a sharpened proximal tip;

an anchor for removably securing at least two suture ends disposed near the proximal end of the needle; and a shield slidably disposed on the shaft to move between a first position in which the sharpened tip is exposed and a second position in which the sharpened tip is covered, wherein the shield lies distally of the sharpened proximal tip of the needle at the first position.

11. The device of claim 10, further comprising a slide connected to the shield, wherein the shield is movable between the first and second positions by movement of the slide.

12. The device of claim 10, wherein the shield includes a proximal surface which is inclined away from the shaft which surface facilitates withdrawal of the device when the shield is in its second position.

13. The device of claim 10, further comprising an indicator on one side of the device.

14. An assembly comprising:

a length of suture;

a surgical suturing device including an elongate shaft having a proximal end and a distal end, an inverted needle attached to the distal end of the shaft and having a sharpened proximal tip, and means including at least one anchor disposed within 5 mm of the sharpened proximal tip for attaching at least two ends of the suture thereto; and wherein the anchor comprises a single aperture and wherein the suture is crossed within the aperture such that one end of the suture can be removed from the needle without dislodging the other end of the suture.

* * * * *